United States Patent
Li et al.

(10) Patent No.: US 10,045,884 B2
(45) Date of Patent: Aug. 14, 2018

(54) NON-WOVEN GAUZE AND METHOD AND SYSTEM FOR MANUFACTURING THE SAME

(71) Applicant: Winner Industries (Shenzhen) Co., Ltd., Shenzhen, Guangdong (CN)

(72) Inventors: Jianquan Li, Guangdong (CN); Huan Wang, Guangdong (CN); Zaoxia Lu, Guangdong (CN)

(73) Assignee: Winner Medical Co., Ltd., Shenzhen (CN)

( * ) Notice: Subject to any disclaimer, the term of this patent is extended or adjusted under 35 U.S.C. 154(b) by 722 days.

(21) Appl. No.: 14/604,156

(22) Filed: Jan. 23, 2015

(65) Prior Publication Data

US 2016/0213520 A1 Jul. 28, 2016

(51) Int. Cl.
*A61F 13/15* (2006.01)
*A61F 13/00* (2006.01)
(Continued)

(52) U.S. Cl.
CPC .. *A61F 13/00051* (2013.01); *A61F 13/00017* (2013.01); *A61F 13/00021* (2013.01);
(Continued)

(58) Field of Classification Search
CPC .......... D04H 18/04; A61F 13/02; A61F 13/44
(Continued)

(56) References Cited

U.S. PATENT DOCUMENTS

| 4,639,253 A * | 1/1987 | Dyer ...................... A61F 13/44 604/362 |
| 5,098,764 A | 3/1992 | Drelich et al. |

(Continued)

FOREIGN PATENT DOCUMENTS

| CN | 102277692 A | 12/2011 |
| CN | 102277692 B | 4/2014 |

(Continued)

OTHER PUBLICATIONS

European Search Report dated Jul. 7, 2015 for EP Application No. 15 15 2391.

(Continued)

*Primary Examiner* — Peter Y Choi
(74) *Attorney, Agent, or Firm* — Ladas & Parry LLP

(57) ABSTRACT

A non-woven gauze product and a method and system for manufacturing same. The spunlace device includes a second spunlace machine having a shaping layer on the surface, the shaping layer is provided with pointed projections having tapered tops disposed in a matrix arrangement, each pointed projection has a bottom of rectangular cross-section, the bottom size of each pointed projection is larger than the bottom distance between two adjacent pointed projections. A non-woven cloth having rectangular holes in an array layout is formed by water jetting the fiber-web at the second spunlace machine. The rectangular holes in an array layout are presented in a flat structure having warp and weft, and the dimension of each rectangular hole is larger than the line width of warp and weft. The features of such non-woven cloth are similar to those of gauze, so the non-woven cloth can be a substitute for the current gauze.

10 Claims, 8 Drawing Sheets

(51) Int. Cl.
*D04H 1/02* (2006.01)
*D04H 1/495* (2012.01)
*D04H 18/04* (2012.01)
*D01G 25/00* (2006.01)

(52) U.S. Cl.
CPC ....... *A61F 13/00987* (2013.01); *D01G 25/00* (2013.01); *D04H 1/02* (2013.01); *D04H 1/495* (2013.01); *D04H 18/04* (2013.01)

(58) Field of Classification Search
USPC .......................................... 442/384; 604/362
See application file for complete search history.

(56) References Cited

U.S. PATENT DOCUMENTS 5,648,141 A * 7/1997 Butterworth ............ A61F 13/36
428/131
2012/0259302 A1* 10/2012 Chaisumdet ............ A61F 13/36
604/367

FOREIGN PATENT DOCUMENTS

EP 1 688 522 A1 8/2006
KR 2006-0090155 A 8/2006

OTHER PUBLICATIONS

Non-English Korean Office Action dated Jun. 12, 2016 for Korean Application No. 2015-0000841.
Espacenet English abstract of CN 102277692 B.

* cited by examiner

NON-WOVEN GAUZE AND METHOD AND SYSTEM FOR MANUFACTURING THE SAME

TECHNICAL FIELD

This invention relates to the field of gauze manufacturing, particularly to a non-woven gauze product and a method and system for manufacturing the same.

PRIOR ART

Gauze is a kind of woven fabric having thin and lightweight warp and weft. Due to its advantages of softness, comfort, excellent breathability, no stimulation to skin, good moisture absorption, strong stretching resistance and no fall-off of fluff, gauze is widely used in medical field. The traditional utilization of gauze covers medical gauze, sticky pad, bandage and breathing mask.

Conventional manufacturing method of gauze is constructed with warp and weft, and gone through a procedure including cotton opening and cleaning, carding, cottonsliver forming, roving forming, spun yarn forming, spooling, warping, slashing, weaving, etc. Such procedure has disadvantages of long production process, complex production, high labor cost, high energy consumption, poor production environment, thread ends at the edge, and the like. Once a thread end is dropped in and even left over in human body in a surgery, it will cause worse of patient's condition. The requirement thus exists to look for a new manufacturing method of gauze.

The non-woven fabric made by current spunlace process has a dense or loose structure. Such fabric having dense structure has shortcomings of hard handfeel, poor drapability and slow speed of imbibition; while fabric having loose structure has shortcomings of having more hairiness on surface, easy pilling, fall-off of fluff, drop-out of fiber and poor strength. Both of these types of spunlace non-woven cloth are not a substitute for the current woven gauze in terms of appearance, texture or performance, especially for applying in medical field due to their shortcomings of slow speed of imbibition, easy pilling or fall-off of fluff.

SUMMARY OF THE INVENTION

According to a first aspect of this invention, a system for manufacturing non-woven gauze product comprising:

a picker for opening, cleaning and blending raw cotton;

a carding machine provided downstream of the picker for further opening and cleaning the raw cotton and carding for fiber-web forming;

a lapping platform provided downstream of the carding machine for spreading the fiber-web in an overlapped manner upon a set specification;

a spunlace device provided downstream of the lapping platform for water jetting the overlapped fiber-web; the spunlace device comprising a first spunlace machine and a second spunlace machine; the first spunlace machine including a first rotatable barrel and a first spunlace support net surrounding the first barrel; the second spunlace machine including a second rotatable barrel and a second spunlace support net surrounding the second barrel, the second spunlace support net having a shaping layer, the shaping layer being provided thereon with pointed projections disposed in a matrix arrangement and a through hole, each pointed projection having a tapered top and a bottom of rectangular cross-section, the bottom size of each pointed projection being larger than the bottom distance between two adjacent pointed projections; and an aftertreatment device provided downstream of the spunlace device for post-processing the product obtained after water jetting process to receive product of non-woven gauze.

According to a second aspect of this invention, a method for manufacturing non-woven gauze product by utilizing the above-mentioned system, comprising:

a picking step for opening, cleaning and blending raw cotton;

a carding step for further opening and cleaning the raw cotton and carding for fiber-web forming;

a lapping step for spreading the fiber-web in an overlapped manner upon a set specification;

a spunlace step for water jetting the overlapped fiber-web introduced into the spunlace device, wherein the spunlace step specifically comprises: prewetting the fiber-web with low-pressure water flow when introducing the fiber-web into the input of the spunlace device; water jetting the prewetted fiber-web with the spunlace device to cause the fiber on the shaping layer of the second spunlace machine to be shifted and entangled under the impact of spunlace to form a rectangular hole on the water-jetted fiber-web; performing water jetting on the fiber-web from the back side thereof by the first spunlace machine, and performing water jetting on the fiber-web from the front side thereof by the second spunlace machine; and an aftertreatment step for post-processing the product obtained after water jetting process to receive product of non-woven gauze.

According to a third aspect of this invention, a non-woven gauze product manufactured by utilizing the above-mentioned system, comprising spunlace non-woven cloth having rectangular holes in an array layout formed by the impact of spunlace, the rectangular holes in an array layout being presented in a flat structure having warp and weft, and the dimension of each rectangular hole being larger than the line width of warp and weft.

With the non-woven gauze product and the manufacturing method and system thereof provided herein, the spunlace device includes a second spunlace machine having a shaping layer on the surface, the shaping layer is provided thereon with pointed projections disposed in a matrix arrangement, each pointed projection has a tapered top and a bottom of rectangular cross-section, the bottom size of each pointed projection is larger than the bottom distance between two adjacent pointed projections. A non-woven cloth having rectangular holes in an array layout is formed by water jetting the fiber-web at the second spunlace machine. The rectangular holes in an array layout are presented in a flat structure having warp and weft, and the dimension of each rectangular hole is larger than the line width of warp and weft. The structure and features of such non-woven cloth are similar to those of gauze, so the non-woven cloth can be a substitute for the current gauze. With this invention, a gauze-like non-woven cloth is achieved by utilizing the disclosed manufacturing process of spunlace non-woven cloth herein, and the corresponding manufacturing method has advantages of short production period and low cost, which reduces the cost of such non-woven gauze product.

DETAILED DESCRIPTION OF THE EMBODIMENTS

The core idea of the present invention is to manufacture gauze by the manufacturing process of spunlace non-woven cloth which has features of short production period, low cost and advanced automation. Since the non-woven gauze manufactured by the manufacturing process disclosed herein has advantages of current gauze, such manufacturing process can be a substitute for current woven gauze process to produce gauze product, which greatly reduces the cost of gauze product.

The current spunlace process, due to the limitation of the structure of spunlace device, can only produce spunlace non-woven cloth having holes in irregular arrangement, which fails to achieve the advantages of gauze.

In an embodiment of the present invention, there is an improvement in the spunlace device, and a spunlace non-woven cloth having advantages of gauze can be produced by rotary drum water jetting.

This invention is further described below in detail with reference to specific embodiments and accompanying drawings.

Embodiment I

Figure 1:
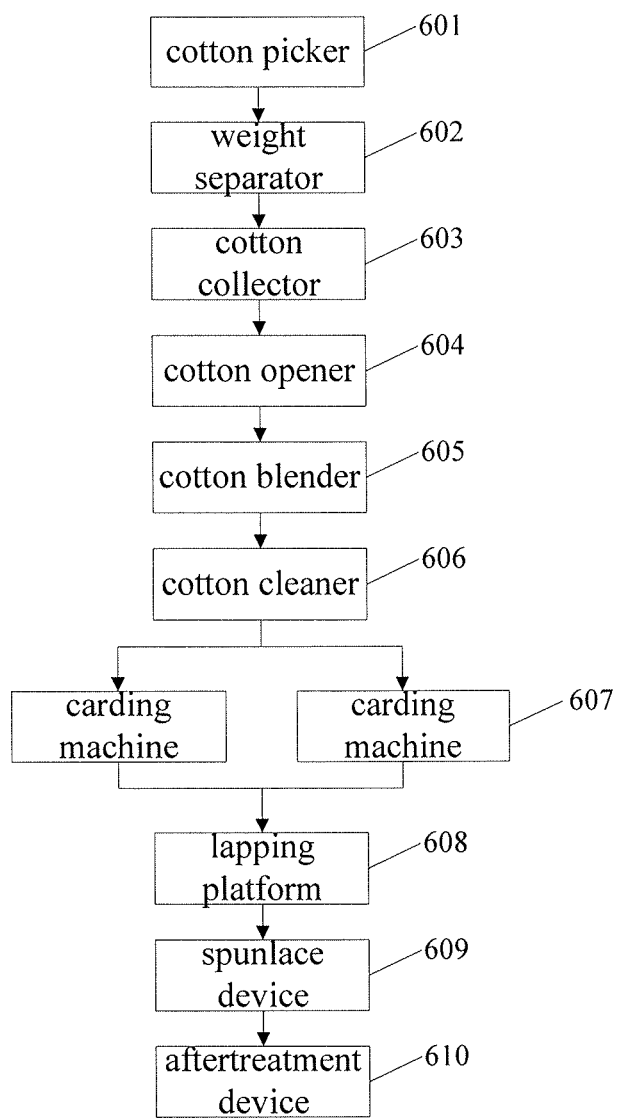
FIG. 1 is a schematic structure chart of the system for manufacturing non-woven gauze product according to an embodiment of this invention.

Referring to FIG. 1, a system for manufacturing non-woven gauze product provided in this embodiment comprises a picker 601, a weight separator 602, a cotton collector 603, a cotton opener 604, a cotton blender 605, a cotton cleaner 606, a carding machine 607, a lapping platform 608, a spunlace device 609 and an aftertreatment device 610.

The cotton picker 601 is used for capturing raw cotton fiber and sending the captured raw cotton fiber to downstream equipment for processing. The piker can be a reciprocating picker and can be applied to various grades of raw cotton and/or cotton-type chemical fiber.

The weight separator 602 is provided downstream of the picker for separating and removing the weight mixed in the raw cotton fiber sent by the picker. In other embodiments, the system for manufacturing non-woven gauze product may further comprise an iron absorption device and a metal-spark-heavy matter diverter, both disposed between the picker and the weight separator. The iron absorption device is located downstream of the picker for checking and removing metal mixed in the raw cotton fiber. The iron absorption device can adopt a bridge-type manner to absorb iron and the like. The metal-spark-heavy matter diverter is located downstream of the iron absorption device for checking and removing metal and heavy matter and preventing a fire.

The cotton collector 603 is located downstream of the weight separator for collecting the raw cotton fiber processed by the weight separator and outputting the collected raw cotton fiber.

The cotton opener 604 is located downstream of the cotton collector for opening and cleaning the raw cotton fiber outputted by the cotton collector. In this embodiment, the cotton opener is a single-stage axial cotton opener.

The cotton blender 605 is located downstream of the cotton opener for blending and loosening the opened raw cotton fiber. In this embodiment, the cotton blender is a multi-bin cotton blender.

The cotton cleaner 606 is located downstream of the cotton blender for fine loosening and cleaning the initially loosened and blended raw cotton fiber.

The carding machine 607 is located downstream of the cotton cleaner for carding the fine loosened and cleaned raw cotton fiber, removing impurities and/or short flocks, and carding for fiber-web forming. In other embodiments, the system for manufacturing non-woven gauze product may further comprise a foreign fiber sorting machine, a dust removing machine, an iron absorption device and a pneumatic hopper cotton feeder, all disposed between the cotton cleaner and the carding machine. The foreign fiber sorting machine is located downstream of the cotton cleaner for removing the foreign fiber mixed in the raw cotton fiber. The dust removing machine is located downstream of the foreign fiber sorting machine for removing tiny impurities mixed in the raw cotton fiber. The iron absorption device is located downstream of the dust removing machine for checking and removing metal mixed in the raw cotton fiber. In an example, the iron absorption device adopts a bridge-type manner to absorb iron and the like. The pneumatic hopper cotton feeder is located downstream of the iron absorption device for evenly feeding the raw cotton fiber into the carding machine.

The lapping platform 608 is located downstream of the carding machine for spreading the fiber-web in an overlapped manner upon a set specification.

It should be noted that, in the lapping platform, the number of layers for spreading the fiber-web in an overlapped manner is determined upon actual demand. Typically, the fiber-web is outputted by utilizing multiple parallel carding machines and spread in an overlapped manner in the lapping platform. FIG. 1 illustrates two carding machines. The number of the carding machine is selected upon the width and weight of fiber. In some embodiments, if there is only one carding machine, the lapping platform only acts as a transport platform without spreading the fiber-web in an overlapped manner. In this embodiment, the lapping platform 608 can adopt a paralleled manner or a staggered manner to spread the fiber-web.

The spunlace device 609 is located downstream of the lapping platform for water jetting the overlapped fiber-web.

Figure 2:
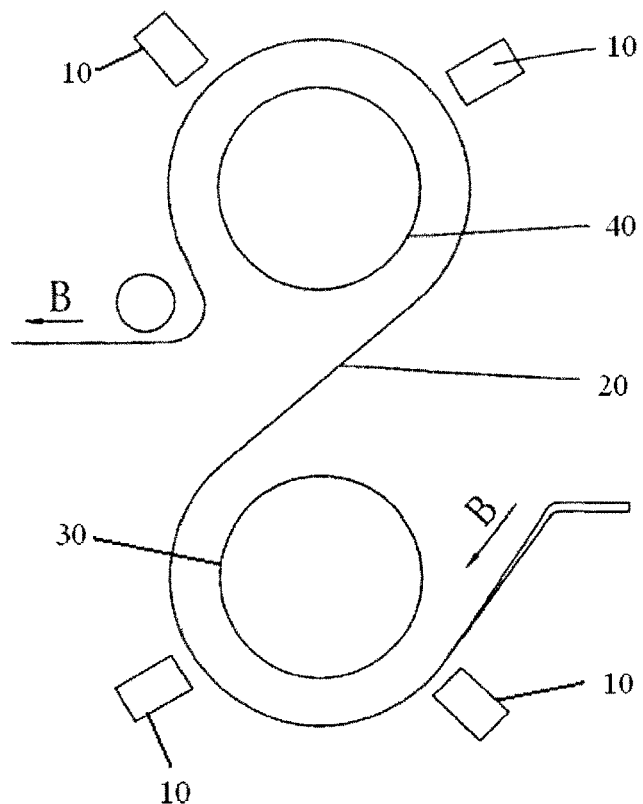
FIG. 2 is a schematic structure drawing of the spunlace device according to an embodiment of this invention.

Referring to FIG. 2, in this embodiment, the spunlace device comprises a first spunlace machine 30 and a second spunlace machine 40.

The first spunlace machine 30 includes a first rotatable barrel and a first spunlace support net 312 surrounding the first barrel; the second spunlace machine 40 includes a second rotatable barrel and a second spunlace support net 412 surrounding the second barrel.

Spunlace heads 10 are arranged along the circumferences of the first and second spunlace machines. Prewetted spunlace heads are disposed at the introduction port of a rotary drum device. The rotary drum is rotated continuously to drive the fiber-web 20 move along the direction B. The first spunlace machine 30 is a rotary drum with function of being entangled by spunlace, and the second spunlace machine 40 is a rotary drum with function of being shaped by spunlace. The fiber-web 20 is passed firstly through the first spunlace machine 30 to be water jetted from back side of the fiber-web, then passed through the second spunlace machine 40 to be water jetted from front side of the fiber-web. To produce a spunlace non-woven having gauze-like structure, the first spunlace machine 30 and the second spunlace machine 40 of the rotary drum device for spunlace non-woven have different rotary drum sleeves, and a rectangular hole is formed during water jetting the fiber-web 20 from the back side.

Figure 3:
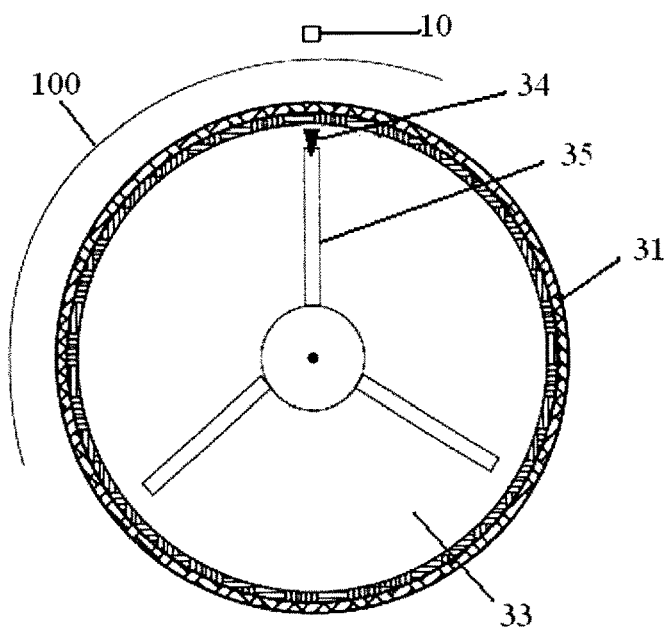
FIG. 3 is a schematic structure drawing of the first spunlace machine in the spunlace device according to an embodiment of this invention.
Figure 4:
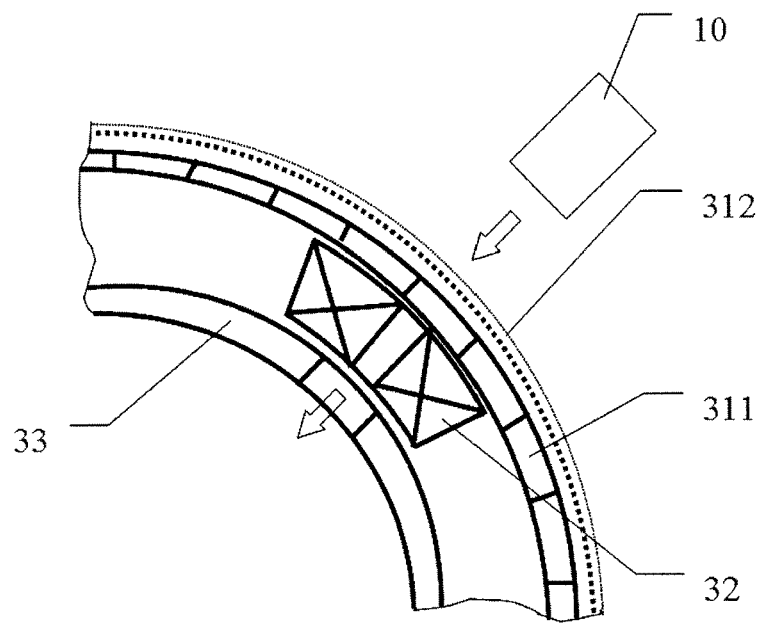
FIG. 4 is a schematic structure drawing of the first spunlace machine in the spunlace device according to an embodiment of this invention.
Figure 5:
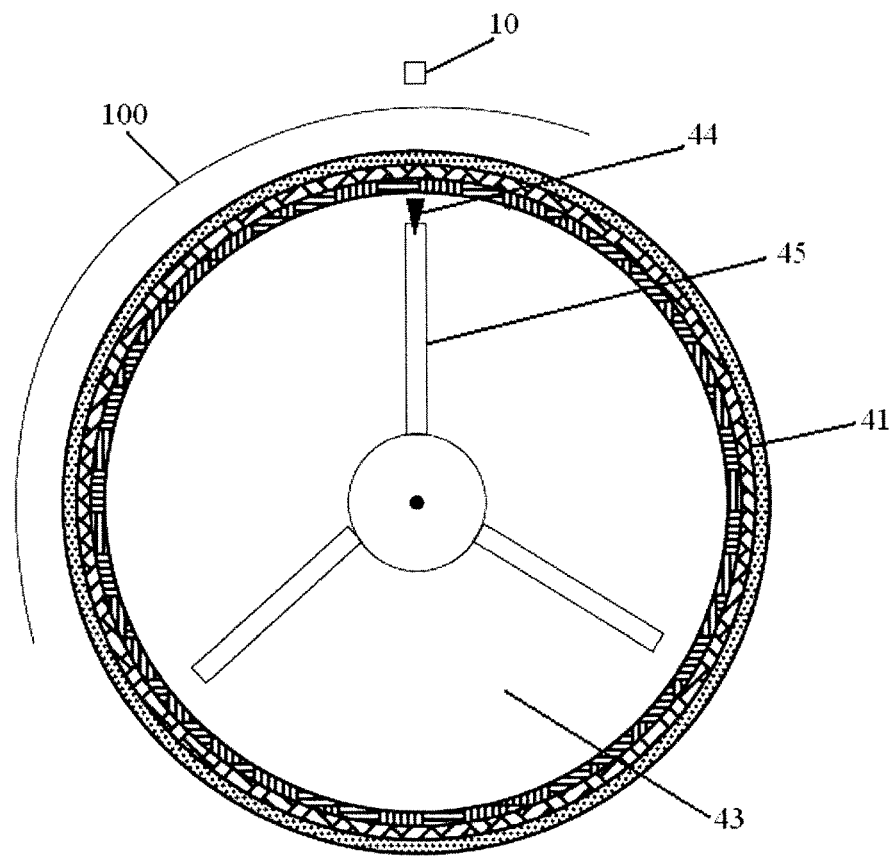
FIG. 5 is a schematic structure drawing of the second spunlace machine in the spunlace device according to an embodiment of this invention.
Figure 6:
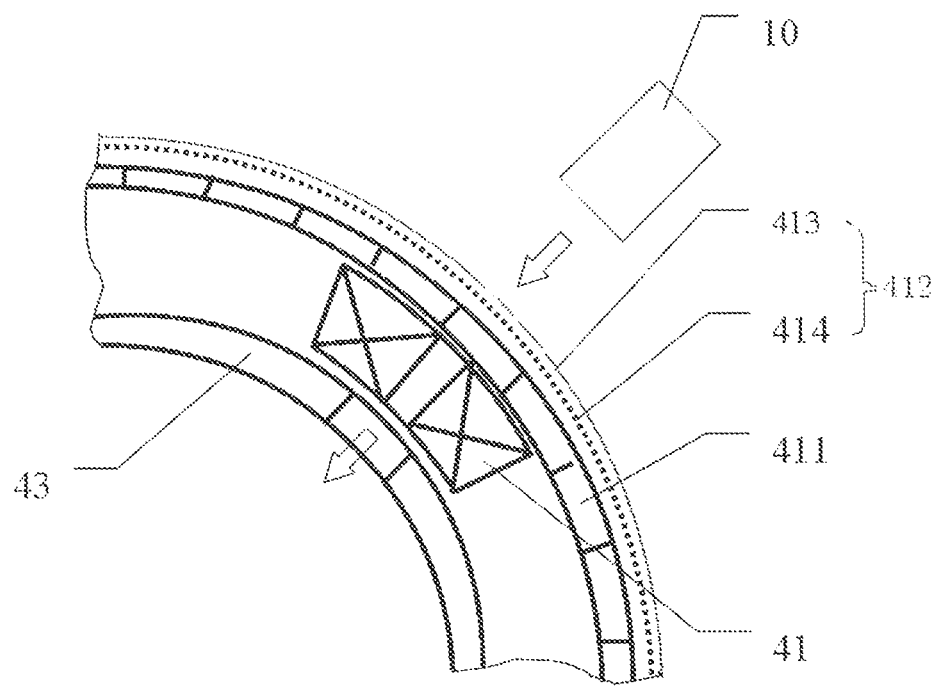
FIG. 6 is a schematic structure drawing of the second spunlace machine in the spunlace device according to an embodiment of this invention.

Referring to FIG. 3 and FIG. 4, the first barrel of the first spunlace machine 30 comprises a first rotary drum sleeve 31, a sealing element 32 and an inner container 33. The first rotary drum sleeve 31 is surrounded the surface of the rotary drum for supporting the fiber-web 100 to be water jetted. One end of the inner container 33 of the rotary drum is connected to a gas-water separator (not shown in the figures). Each spunlace head 10 is respectively provided with a suction port 34 of a suction groove. The suction port 34 is communicated with a support frame 35. The suction port 34 and the support frame 35 form a negative pressure suction system or part of the negative pressure system, which is used for drawing water from the fiber-web 100 and the first rotary drum sleeve 31. The sealing element 32 is mounted between the inner container 33 and the first rotary drum sleeve 31 and used for sealing and holding the first rotary drum sleeve 31. The first rotary drum sleeve 31 comprises a first rotary drum sleeve barrel 311. The first spunlace support net 312 is disposed outside the first rotary drum sleeve barrel 311. The first spunlace support net 312 is used for supporting the fiber-web for water jetting. The first rotary drum sleeve barrel 311 can be a steel plate having drilled holes or a honeycomb net rolled into a cylinder. The first spunlace support net 312 can be a stainless steel wire net or a nickel wire net. The first spunlace support net 312 can also be a double-layer net, for example an overlapped double-layer net with a stainless steel wire net and a nickel wire net. When the rotary drum works, the inner container 33 is kept to be immovable, while the first rotary drum sleeve 31 is revolved. The spunlace heads 10 inject water flow to the surface of the first spunlace support net 312 along the arrow direction as shown in FIG. 4.

Referring to FIGS. 5-9, the second barrel of the second spunlace machine 40 (i.e. rotary drum with function of being shaped by spunlace) comprises a second rotary drum sleeve 41, a sealing element 42 and an inner container 43. A suction port 44 for collecting water flow is provided inside the second rotary drum sleeve 41. The suction port 44 is communicated with a support frame 45. The second rotary drum sleeve 41 comprises a second rotary drum sleeve barrel 411. The second spunlace support net 412 is disposed outside the second rotary drum sleeve barrel 411.

The second rotary drum sleeve barrel 411 is a punching hole mesh rolled into a cylinder, for example the barrel is made of a sheet of stainless steel on which holes are punched. The second rotary drum sleeve barrel 411 clings to the inner surface of the second spunlace support net 412 to support the second spunlace support net 412, so that the second spunlace support net 412 can withstand pressure during spunlace negative pressure suction to better pump water away, thus better entangling fiber on the second spunlace support net 412.

Figure 7:
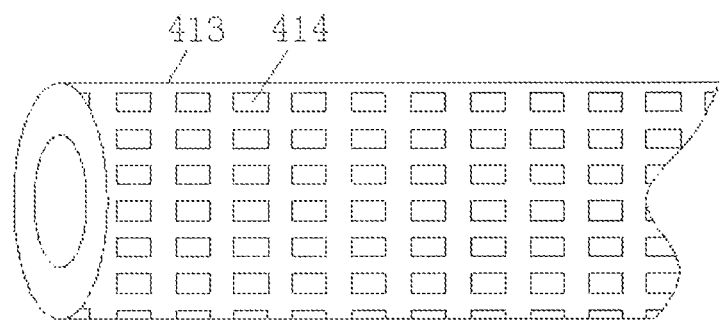
FIG. 7 is a schematic structure drawing of the second spunlace support net of the second spunlace machine in the spunlace device according to an embodiment of this invention.
Figure 8:
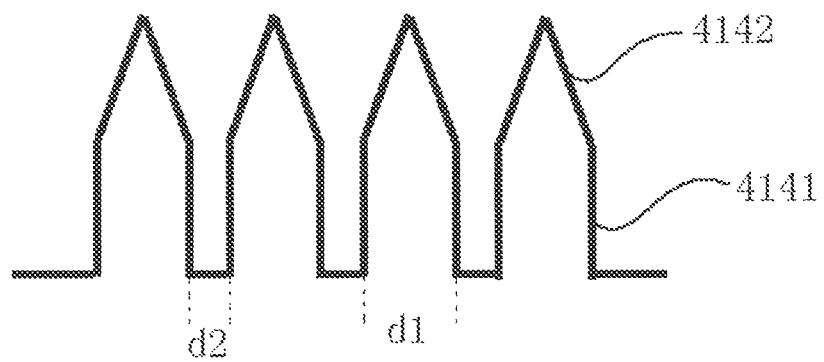
FIG. 8 is a schematic structure drawing of pointed projections on the shaping layer in the second spunlace machine of the spunlace device according to an embodiment of this invention.
Figure 9:
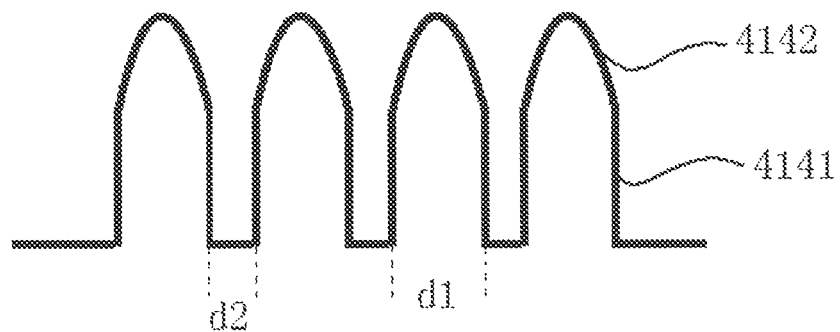
FIG. 9 is a schematic structure drawing of pointed projections on the shaping layer in the second spunlace machine of the spunlace device according to an embodiment of this invention.

Referring to FIGS. 7-9, the second spunlace support net 412 comprises a shaping layer 413 provided with thereon with pointed projections 414 disposed in a matrix arrangement and a through hole, each pointed projection 414 has a tapered top and a bottom of rectangular cross-section, the bottom size (d1) of each pointed projection 414 is larger than the bottom distance (d2) between two adjacent pointed projections. The bottom size of each pointed projection 414 refers to the long and wide of the rectangular cross-section at the bottom of the pointed projection 414. The bottom distance between two adjacent pointed projections refers to the vertical interval between an edge of the pointed projection 414 and an edge of adjacent pointed projection close thereto. As shown in FIG. 8 and FIG. 9, the distance d1 is larger than the distance d2.

The shaping layer 413, functioned as forming rectangular holes required by spunlace non-woven, is located at the surface layer of the second spunlace support net 412. Referring to FIG. 8 and FIG. 9, the pointed projection 414 comprises a cuboid portion 4141 at its lower end and a tip portion 4142 at its upper end. FIG. 8 and FIG. 9 show two different shapes of the tip portion 4142; however, in other embodiments, the shape can also be properly changed according to actual requirement. The tip portion 4142 forms the tapered top of the pointed projection, which makes it easier to form rectangular holes on the fiber-web during water jetting.

In this embodiment, the bottom distance between two adjacent pointed projections is 0.1~1 mm, the density of the pointed projections on the shaping layer 414 is not less than 50 per square inch, for example, choosing 75 per square inch to manufacture gauze product having sparser structure.

Figure 10:
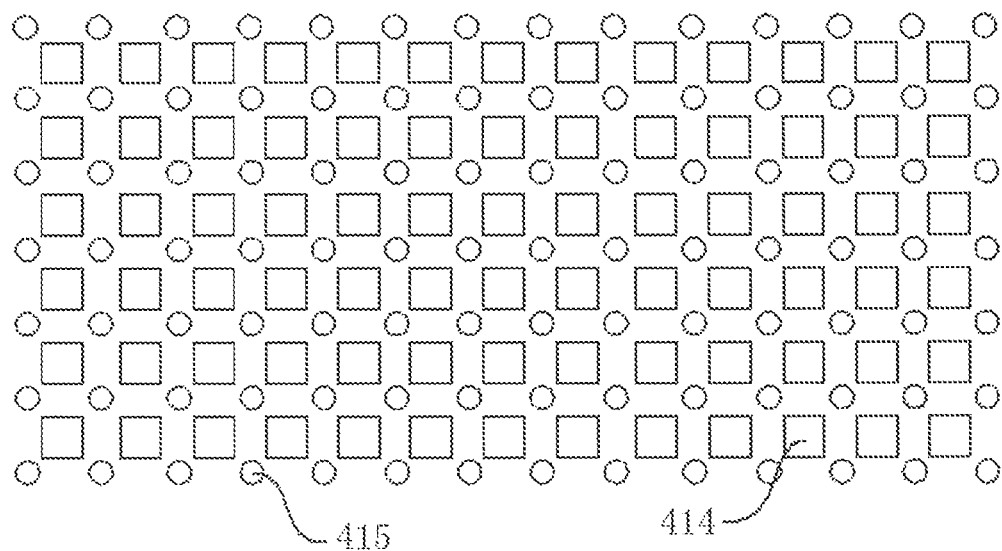
FIG. 10 is a schematic side view from outside of the second spunlace machine in the spunlace device according to an embodiment of this invention.
Figure 11:
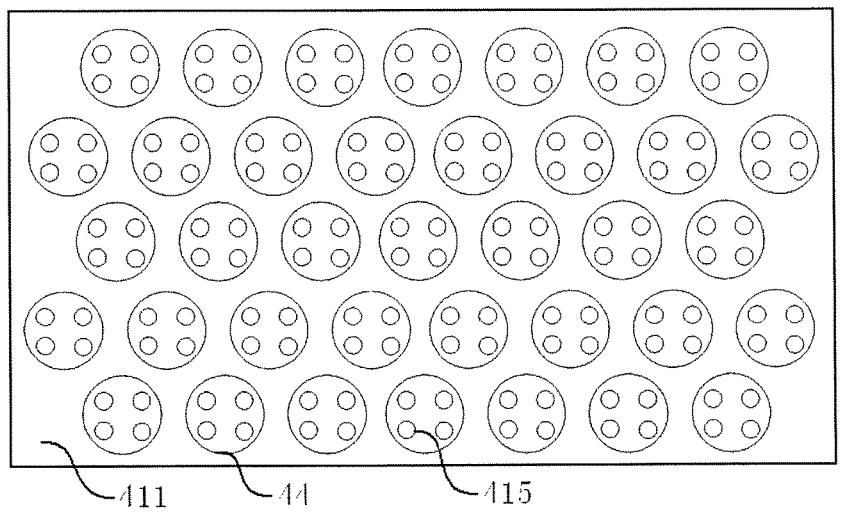
FIG. 11 is a schematic side view from inside of the second spunlace machine in the spunlace device according to an embodiment of this invention.

Referring to FIG. 10 and FIG. 11, FIG. 10 shows a side view from outside of the second rotary drum sleeve 41, and FIG. 11 shows a side view from inside of the second rotary drum sleeve 41.

Each pointed projection 414 on the shaping layer 413 is provided around with through holes 415 for pumping wastewater after water jetting. The suction port 44 is communicated with the through holes 415. The through holes are not marked in FIG. 7.

The shaping layer 413 is made from polyester polymer or metal material, such as polycarbonate material. The pointed projections 414 on the shaping layer 413 can be made by casting process.

Figure 12:
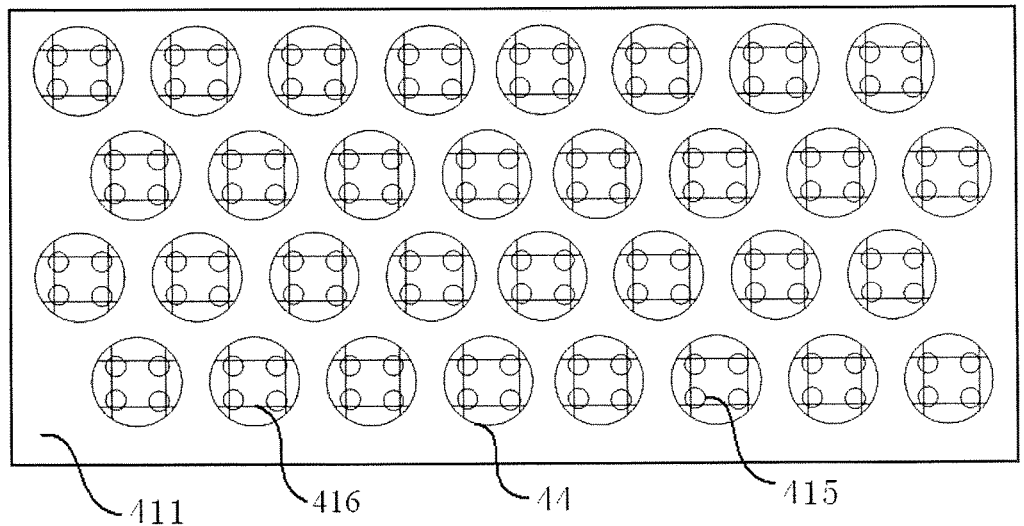
FIG. 12 is a schematic side view from inside of the second spunlace machine in the spunlace device according to another embodiment of this invention.

FIG. 12 shows a side view from inside of the second rotary drum sleeve 41 according to another embodiment. The spunlace support net 412 may further comprise a rebounding layer 416 clung to the inner surface of the shaping layer 413. The rebounding layer 416 is a metal wire net, for example a stainless steel wire net. The rebounding layer 416 is used to prevent fiber from entering into the suction port 44 with water flow of spunlace. Moreover, the water flow jetted across fiber is slightly rebounded by the rebounding layer 416, which makes the fiber entangled better with the shaping layer 413. The second spunlace support net 412, the rebounding layer 416 and the second rotary drum sleeve barrel 411 are successively combined without misplacement. The dimension of an opening of the rebounding layer 416 is larger than that of the through hole 415, which makes a better effect on rebounding the water flow. The thickness of the second rotary drum sleeve barrel 411 is larger than that of the second spunlace support net 412 and the rebounding layer 416, which plays a good role in supporting function.

In this embodiment, the pointed projections 414 each having a tapered top, provided on the shaping layer 413 of the second spunlace machine 40, form rectangular holes arranged regularly in a matrix manner on the fiber-web during water jetting. The cotton fiber entangled between adjacent rectangular holes forms a crisscrossed structure of warp and weft. Since there is no overlap between warp and weft, the shaping layer 413 is flat except the projections and through holes. Therefore, a flat structure of warp and weft is presented on the spunlace non-woven, and the long and wide of each rectangular hole is respectively larger than the width of warp and weft, which enhances the softness and hydroscopicity of the spunlace non-woven, thus such newly spunlace non-woven achieves a gauze-like effect.

The aftertreatment device 610 is located downstream of the spunlace device for post-processing the product obtained after water jetting process to receive non-woven gauze product. The aftertreatment device can comprise a degreasing and bleaching device, a dryer, a coiler, a cutter and the like.

Figure 13:
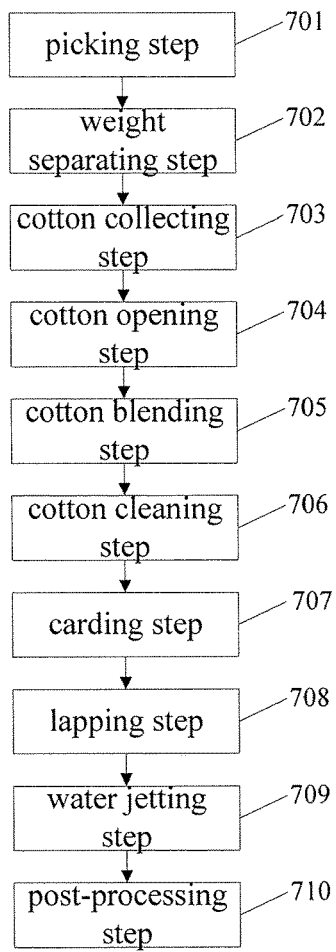
FIG. 13 is a schematic flow chart of the method for manufacturing non-woven gauze product according to an embodiment of this invention.

Referring to FIG. 13, a method for manufacturing non-woven gauze product by utilizing the above-mentioned system provided correspondingly in this embodiment comprises:

Step 701, picking cotton, that is, capturing raw cotton fiber and sending the captured raw cotton fiber to downstream equipment for processing. The raw cotton fiber is typically an all-cotton material.

Step 702: weight separating, that is, separating and removing the weight mixed in the raw cotton fiber sent by the picker.

Step 703: cotton collecting, that is, collecting the raw cotton fiber.

Step 704: cotton opening, that is, opening and cleaning the collected raw cotton fiber.

Step 705: cotton blending, that is, blending and loosening the opened raw cotton fiber.

Step 706: cotton cleaning, that is, fine loosening and cleaning the initially loosened and blended raw cotton fiber.

Step 707: carding, that is, carding the fine loosened and cleaned raw cotton fiber, removing impurities and/or short flocks, and carding for fiber-web forming.

Step 708: lapping, that is, spreading the fiber-web in an overlapped manner upon a set specification. It should be noted that, in the lapping step, the number of layers for spreading the fiber-web in an overlapped manner is determined upon actual demand. Typically, the fiber-web is outputted by utilizing multiple parallel carding machines and spread in an overlapped manner in the lapping platform. In some embodiments, if there is only one carding machine, the lapping platform only acts as a transport platform without spreading the fiber-web in an overlapped manner in the lapping step. In this embodiment, at the lapping step, a paralleled manner or a staggered manner to spread the fiber-web can be adopted.

Step 709: water jetting, that is, water jetting the overlapped fiber-web in the spunlace device in the above-mentioned Embodiment I. This step specifically comprises: prewetting the fiber-web with low-pressure water flow when introducing the fiber-web into the input of the spunlace device; water jetting the prewetted fiber-web with the spunlace device to cause the fiber on the shaping layer of the second spunlace machine to be shifted and entangled under the impact of spunlace to form rectangular holes on the water-jetted fiber-web; performing water jetting on the fiber-web from the back side thereof by the first spunlace machine, and performing water jetting on the fiber-web from the front side thereof by the second spunlace machine. In this embodiment, water jetting along vertical direction is adopted with a spunlace pressure of 40~500 bar.

Step 710: post-processing, that is, post-processing the product obtained after water jetting process to receive non-woven gauze product. Such aftertreatment step may comprise steps of degreasing and bleaching, softening and finishing, drying, coiling, cutting, etc.

Figure 14:
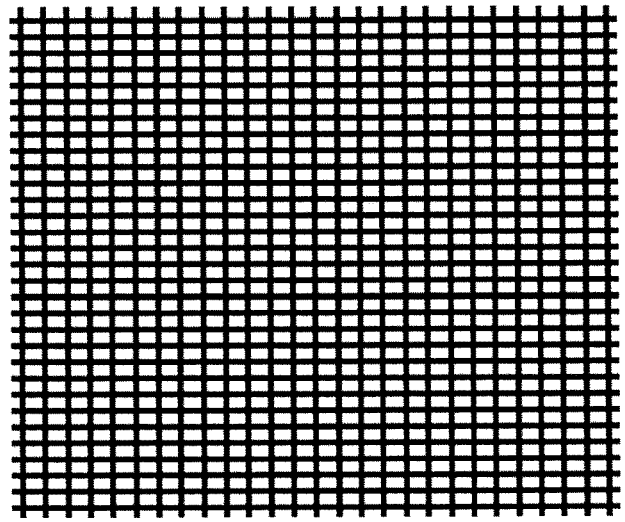
FIG. 14 is a schematic structure drawing of the non-woven gauze product according to an embodiment of this invention.

Referring to FIG. 14, a non-woven gauze product manufactured by the above-mentioned method provided correspondingly in this embodiment comprises spunlace non-woven cloth. The spunlace non-woven cloth has rectangular holes in an array layout formed by the impact of spunlace. The rectangular holes in an array layout are presented in a flat structure having warp and weft. The dimension of each rectangular hole is larger than the line width of warp and weft. The dimension of the rectangular hole refers to the long and wide of the rectangular hole. To achieve a better gauze-like effect, the line width of warp and weft of the non-woven gauze is 0.1~1 mm. The warp/weft density refers to the number of warp/weft per inch. The density of the rectangular holes refers to the number of the rectangular holes per square inch. The density of the rectangular holes is not less than 50 holes per square inch, for example, 75 holes per square inch. Specifically, the warp/weft density of the non-woven gauze product may be chosen as 19*15 per inch or 30*20 per inch. Generally, the holes on a sheet of gauze are holes of relatively rigid rectangle. As for the non-woven gauze provided in this embodiment, the rectangular holes thereof are rigidly rectangular holes. Therefore the non-woven gauze has gauze-like effect as well as gauze-like structure and features. The non-woven gauze product can be used as a medical dressing formed by superimposing multiple layers of spunlace non-woven cloth.

Embodiment II

Figure 15:
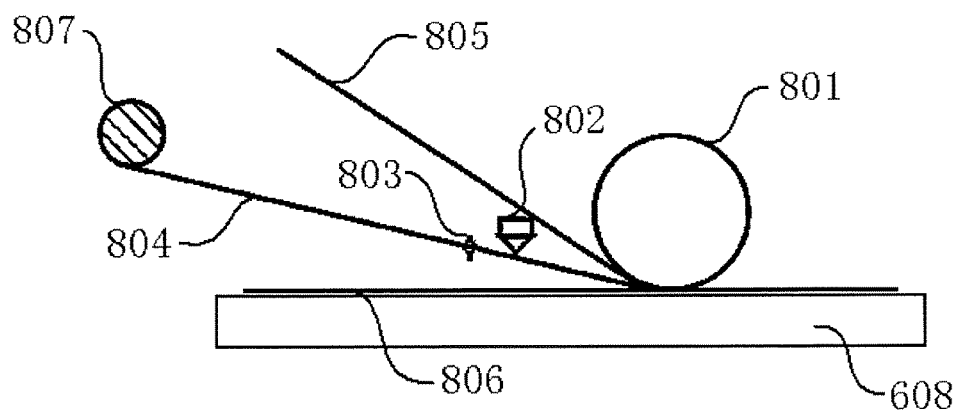
FIG. 15 is a schematic structure drawing of local structure of the system for manufacturing non-woven gauze product according to another embodiment of this invention.

Referring to FIG. 15, another kind of system for manufacturing non-woven gauze product is provided in this embodiment. The difference between this embodiment and Embodiment I is that, the system of this embodiment further comprises a sensing line transporter 807 for transporting a sensing line 804 to the lapping platform 608 and to a place between upper and lower fiber-webs delivered by one or more carding machine. The lapping platform 608 is provided with a press roller 801 for pressing the sensing line 804 delivered by the sensing line transporter to the place between the upper fiber-web 805 and lower fiber-web 806 when spreading the fiber-web in an overlapped manner. The sensing line transporter 807 can be an unwinding device.

A double doffer carding machine is generally adopted, which can output two layers of fiber-web. In some embodiments, if only one carding machine is adopted in the system for manufacturing non-woven gauze product, the two layers of fiber-web outputted by the carding machine are served as an upper fiber-web and a lower fiber-web delivered to the lapping platform. If there are two or more carding machines adopted in the system for manufacturing non-woven gauze, the two layers of fiber-web outputted by each carding machine are firstly combined together as one layer of fiber-web, then the combined fiber-web from one or more carding machines is served as the lower fiber-web delivered to the lapping platform, and the combined fiber-web from the rest carding machines is served as the upper fiber-web delivered to the lapping platform. In this embodiment, there are two carding machines shown in FIG. 1, wherein the two layers of fiber-web outputted by one carding machine are combined together as one layer which is served as the lower fiber-web delivered to the lapping platform, and the two layers of fiber-web outputted by the other carding machine are combined together as one layer which is served as the upper fiber-web delivered to the lapping platform.

Due to the need to ensure the sensing line straightly embedded between two layers of fiber-web, only the paralleled manner to spread the fiber-web can be adopted in the lapping platform 608 in this embodiment.

Once the sensing line is shifted under the impact of water flow during spunlace process, the sensing line will be bent and not straight on non-woven cloth, which will affect subsequent cutting process. In order to make the embedded sensing line to be kept stable between the two layers of fiber-web without shifting to prevent the sensing line from shifting under the impact of water flow during spunlace process, the system for manufacturing non-woven gauze product further comprises a coater 802 for coating adhesive on the sensing line prior to embedding the sensing line into the place between the upper and lower fiber-webs. The sensing line will closely stick to the fiber-web after coated by the coater and pressed by the press roller. Hence, during spunlace process, when fiber is entangled and shifted under the impact of water flow, the fiber stuck to the sensing line is moved to one side integrally due to the constraint of the sensing line, such that the sensing line is still remained to be a straight line, which will not affect the appearance of the non-woven cloth as well as subsequent cutting process. To coat adhesive on the sensing line, a spraying or paint method can be adopted. Moreover, when coating adhesive on a sensing line, it can be performed in a manner of coating upon an preset interval, so as to protect the softness of non-woven cloth from the effect of adhesive.

When the sensing line between the upper and lower layers of fiber-web is pressed with the press roller, the sensing line may be moved relative to the two layers of fiber-web due to vibration of mechanical equipment, which may affect the straightness of the pressed sensing line. To ensure the embedded sensing line more straight, a metal ring 803 is provided ahead of the coater in the system for manufacturing non-woven gauze product. The sensing line is threaded through the metal ring 803. When the sensing line between the upper and lower layers of fiber-web is pressed with the press roller, the movement of the sensing line is restrained due to the fixation on the sensing line by the metal ring 803, thus ensuring the straightness of the sensing line. There can be one metal ring, or a series of multiple metal rings arranged in a cascaded manner. The metal ring can be secured to one end of a fixed link, and the other end of the fixed link is secured to the lapping platform. The end of the fixed link secured on the lapping platform can be provided with a rotatable structure. The position of the metal ring can be adjusted by adjusting the fixed link, thus adjusting the track of the chip-binding wire (which will be described hereinafter).

After embedding the sensing line at the lapping platform, the combined fiber-web is immediately delivered to the spunlace device. To ensure the sensing line be presented as a straight line on the shaped spunlace cloth, the first spunlace head is disposed as closest as possible to the press roller.

With the system for manufacturing non-woven gauze product provided in this embodiment, a sensing line can be embedded into gauze having rectangular holes. There can be one embedded sensing line, or more embedded sensing lines arranged parallelly upon a preset interval. When embedding a plurality of sensing lines, a plurality of sensing line transporters are needed correspondingly to deliver a plurality of sensing lines parallelly upon a preset interval to the place between upper fiber-web and lower fiber-web.

Another method for manufacturing non-woven gauze product by utilizing the above-mentioned system is provided correspondingly in this embodiment. The difference between this embodiment and Embodiment I is that the step 708 (i.e. lapping step) further comprises a step of embedding a sensing line between two layers of fiber-web.

In order to make the embedded sensing line stable between the two layers of fiber-web without shifting, the lapping step further comprises a step of coating adhesive on the sensing line prior to embedding the sensing line into the place between the upper and lower fiber-webs. The sensing line will closely stick to the fiber-web after being coated by the coater and pressed by the press roller. To coat adhesive on the sensing line, a spraying or paint method can be adopted.

With the method for manufacturing non-woven gauze product provided in this embodiment, a sensing line can be embedded into gauze having rectangular holes. There can be one embedded sensing line, or more embedded sensing lines arranged parallelly upon a preset interval. Due to the need to ensure the sensing line be straightly embedded between two layers of fiber-web, only the paralleled manner to spread the fiber-web can be adopted in the lapping step in this embodiment.

Figure 16:
FIG. 16 is a schematic structure drawing of the non-woven gauze product according to another embodiment of this invention.

Referring to FIG. 16, another non-woven gauze product manufactured by the method of this embodiment is provided correspondingly in this embodiment. The difference between this embodiment and Embodiment I is that a sensing line 901 is embedded between two layers of the spunlace non-woven cloth. The sensing line 901 is embedded between the fiber of the spunlace non-woven cloth, and the upper and lower surfaces thereof are covered by entangled fibers. There can be one or more embedded sensing lines. As shown in FIG. 16, the label 902 represents non-woven layer.

The sensing line can be a X-Ray detectable thread or a chip-binding wire bound with a chip capable of transmitting radio signals (e.g. radio-frequency signals).

The X-ray detectable thread can be fiber coated with X-ray absorption material (e.g. barium sulfate).

Figure 17:
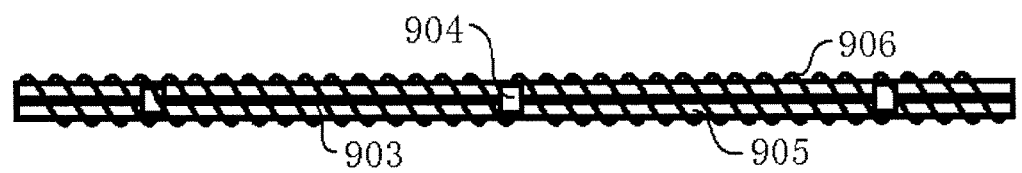
FIG. 17 is a schematic structure drawing of the chip-binding wire according to another embodiment of this invention.

In this embodiment, the sensing line is a chip-binding wire. Referring to FIG. 17, the chip-binding wire comprises a metal wire 903, a chip 904, a non-woven layer 905 and a fixing thread 906.

One or more chips 904 arranged upon a preset interval are fixed on the metal wire 903. The non-woven layer 905 is wrapped around the outside of the metal wire 903 and the chip 904. The fixing thread 906 is wound around the outside of the non-woven layer 905.

To protect the non-woven gauze product from the effect of the thickness of the chip-binding wire, the metal wire 903 is tiny, for example adopting a copper wire. Furthermore, the metal wire is a continuous copper wire or a plurality of end-to-end binding copper wire sections. In the case that the metal wire is a plurality of end-to-end binding copper wire sections, each section is provided with at least a chip, and that when only one chip, the chip can be disposed at the midpoint of the copper wire section. The chip 904 can emit radio signals. Each chip has a correspondingly independent serial number which can be detected by a receiver used for receiving radio wave. The distance between two chips can be set according to actual requirement, for instance 29 cm. The chip is cohered to the metal wire by conducting resin, and the metal wire can act as an antenna, thereby increasing the detection distance of the chip.

To guarantee the fixing thread 906 to be more securely wrapped around the outside of the non-woven layer 905, the fixing thread 906 is combined therein with at least one thread of spandex. The fixing thread 906 can be formed of multiple yarns, and the spandex thread is combined inside the multiple yarns. The elasticity of the spandex thread is higher than that of normal yarn, thus improving the elasticity of the fixing thread and making the wrapped thread more solid.

It is noted that, during the manufacturing process of the non-woven gauze, after embedding the chip-binding wire, when cutting the spunlace non-woven gauze into small pieces, it is usually to ensure that each piece of gauze has only one chip-binding wire and only one chip.

The non-woven gauze product provided in this embodiment can be a medical dressing formed by superimposing multiple layers of spunlace non-woven cloth. If the medical dressing is dropped in human body during surgery, it can easily be checked out because of the embedded sensing line, so as to avoid the occurrence of medical malpractice.

The above are further detailed descriptions about this invention in combination with specific embodiments, but it cannot be concluded that specific implementation of this invention is merely limited to such descriptions. Persons of ordinary skill in the art also can made simple deductions or replacements without departing from the concept of this invention, which should be regarded as falling within the protection scope of this invention.

What is claimed is:

1. A system for manufacturing non-woven gauze product, comprising:
   a picker for opening, cleaning and blending raw cotton;
   a carding machine provided downstream of the picker for further opening and cleaning the raw cotton and carding for fiber-web forming;
   a lapping platform provided downstream of the carding machine for spreading the fiber-web in an overlapped manner upon a set specification;
   a sensing line transporter for transporting a sensing line to the lapping platform and to a place between upper and lower fiber-webs delivered by one or more carding machine, wherein said sensing line is a chip-binding wire bound with a chip capable of transmitting radio signals which chip-binding wire comprises:
   a metal wire;
   one or more chips arranged upon a preset interval and fixed on the metal wire;
   a non-woven layer wrapped around the metal wire and the chip; and
   a fixing thread wound around the non-woven layer;
   the lapping platform being provided with a press roller for pressing the sensing line delivered by the sensing line transporter to the place between the upper and lower fiber-webs when spreading the fiber-web in an overlapped manner;
   a spunlace device provided downstream of the lapping platform for water jetting the overlapped fiber-web; the spunlace device comprising a first spunlace machine and a second spunlace machine; the first spunlace machine including a first rotatable barrel and a first spunlace support net surrounding the first barrel; the second spunlace machine including a second rotatable barrel and a second spunlace support net surrounding the second barrel, the second spunlace support net having a shaping layer, the shaping layer being provided thereon with pointed projections disposed in a matrix arrangement and a through hole, each pointed projection having a tapered top and a bottom of rectangular cross-section, the bottom size of each pointed projection being larger than the bottom distance between two adjacent pointed projections; and
   an aftertreatment device provided downstream of the spunlace device for post-processing the product obtained after water jetting process to receive non-woven gauze product.

2. The system according to claim 1, wherein the bottom distance between two adjacent pointed projections is 0.1~1 mm, the density of the pointed projections on the shaping layer is not less than 50 per square inch.

3. The system according to claim 1, further comprising a coater for coating adhesive on the sensing line prior to embedding the sensing line into the place between the upper and lower fiber-webs.

4. The system according to claim 3, further comprising a metal ring provided ahead of the coater for fixing the sensing line.

5. A method for manufacturing non-woven gauze product by utilizing the system according to claim 1, comprising:
   a picking step for opening, cleaning and blending raw cotton;
   a carding step for further opening and cleaning the raw cotton and carding for fiber-web forming;
   a lapping step for spreading the fiber-web in an overlapped manner upon a set specification, wherein the lapping step further comprises: embedding the sensing line into a place between two layers of fiber-web wherein said sensing line is a chip-binding wire bound with a chip capable of transmitting radio signals which chip-binding wire comprises:

a metal wire;
one or more chips arranged upon a preset interval and fixed on the metal wire;
a non-woven layer wrapped around the metal wire and the chip; and
a fixing thread wound around the non-woven layer;
a spunlace step for water jetting the overlapped fiber-web introduced into the spunlace device, wherein the spunlace step specifically comprises: prewetting the fiber-web with low-pressure water flow when introducing the fiber-web into the input of the spunlace device; water jetting the prewetted fiber-web with the spunlace device to cause the fiber on the shaping layer of the second spunlace machine to be shifted and entangled under the impact of spunlace to form a rectangular hole on the water-jetted fiber-web; performing water jetting on the fiber-web from the back side thereof by the first spunlace machine, and performing water jetting on the fiber-web from the front side thereof by the second spunlace machine; and
an aftertreatment step for post-processing the product obtained after water jetting process to receive product of non-woven gauze.

6. The method according to claim 5, wherein in the lapping step, prior to embedding the sensing line into a place between two layers of fiber-web, further comprises:
coating adhesive on the sensing line.

7. A non-woven gauze product comprising spunlace non-woven cloth having rectangular holes in an array layout formed by the impact of spunlace, the rectangular holes in an array layout being presented in a flat structure having warp and weft, and the dimension of each rectangular hole being larger than the distance between adjacent rectangular holes;
said product further comprising a sensing line embedded among the fibers of the spunlace non-woven cloth, wherein said sensing line is a chip-binding wire bound with a chip capable of transmitting radio signals which chip-binding wire comprises:
a metal wire;
one or more chips arranged upon a preset interval and fixed on the metal wire;
a non-woven layer wrapped around the metal wire and the chip; and
a fixing thread wound around the non-woven layer;
and the upper and lower surfaces thereof being covered by entangled fibers.

8. The non-woven gauze product according to claim 7, wherein the distance between adjacent rectangular holes of the non-woven gauze product is 0.1~1 mm, and the density of the rectangular holes is not less than 50 per square inch.

9. The non-woven gauze product according to claim 7, wherein the metal wire is a continuous copper wire or a plurality of end-to-end binding copper wire sections, and/or the fixing thread is combined therein with at least one thread of spandex.

10. The non-woven gauze product according to claim 7, wherein the non-woven gauze product is a medical dressing.

* * * * *